United States Patent
Yang et al.

(10) Patent No.: US 9,687,276 B2
(45) Date of Patent: Jun. 27, 2017

(54) SKIN REMOVING IMPLEMENT

(75) Inventors: Jun Yang, Zhejiang (CN); Ajit Khubani, Fairfield, NJ (US)

(73) Assignee: INTERNATIONAL EDGE INC., Fairfield, NJ (US)

( * ) Notice: Subject to any disclaimer, the term of this patent is extended or adjusted under 35 U.S.C. 154(b) by 1189 days.

(21) Appl. No.: 12/074,603

(22) Filed: Mar. 4, 2008

(65) Prior Publication Data

US 2009/0071491 A1    Mar. 19, 2009

Related U.S. Application Data

(63) Continuation-in-part of application No. 29/292,718, filed on Oct. 25, 2007, now abandoned, and a continuation-in-part of application No. 29/292,719, filed on Oct. 25, 2007, now abandoned.

(30) Foreign Application Priority Data

Sep. 14, 2007  (CN) .......................... 2007 3 0309021

(51) Int. Cl.
| | |
|---|---|
| *A61B 17/50* | (2006.01) |
| *A61B 17/54* | (2006.01) |
| *A61B 17/32* | (2006.01) |

(52) U.S. Cl.
CPC ...... *A61B 17/54* (2013.01); *A45D 2200/1054* (2013.01); *A61B 2017/320008* (2013.01)

(58) Field of Classification Search
CPC .......... A61B 17/54; A61B 2017/00761; A61B 2017/320004; A61B 2017/320008; A47J 43/25

USPC ....... 606/131; 30/127, 27; 604/290, 22, 289; 451/87, 88, 344; 132/73, 73.5, 75.3, 132/75.5, 76.2, 76.5
See application file for complete search history.

(56) References Cited

U.S. PATENT DOCUMENTS

| | | |
|---|---|---|
| 107,808 A | 9/1880 | Phillips |
| 297,816 A | 4/1884 | Ledward |
| 788,236 A | 4/1905 | Bartholomew |
| 852,873 A | 5/1907 | Davidson |
| 1,498,156 A | 6/1924 | Drew |

(Continued)

FOREIGN PATENT DOCUMENTS

| | | |
|---|---|---|
| DE | 3320594 | 12/1984 |
| DE | 19624578 | 1/1998 |

(Continued)

OTHER PUBLICATIONS

Kauffmann, Stephane. "Intellimouse Wireless Explorer" Oct. 26, 2001. Tom's Harrdware Guide.*

(Continued)

*Primary Examiner* — Katherine M Shi

(74) *Attorney, Agent, or Firm* — Cooper & Dunham LLP

(57) ABSTRACT

A device for removing skin having a cartridge with a file containing a plurality of cutting edges for scraping skin, wherein the cartridge is connected to a handle such that the removed skin is collected between the cartridge and the handle, and a removable cover that may be connected to the cartridge by placing the cover over the cutting surface so as to shield the user from the cutting surface when the implement is not in use and/or to prevent removed skin from exiting the cartridge through the cutting surface.

1 Claim, 7 Drawing Sheets

(56) References Cited

U.S. PATENT DOCUMENTS

| | | | |
|---|---|---|---|
| 1,714,371 A | | 5/1929 | Jackson |
| 2,573,487 A | | 10/1951 | Potvin |
| D167,270 S | | 7/1952 | Marcus |
| 2,612,683 A | | 10/1952 | Potvin |
| 2,615,486 A | * | 10/1952 | Marcus .................. 241/168 |
| 2,714,908 A | | 8/1955 | Carmack |
| 2,746,461 A | * | 5/1956 | Bocchino .................. 132/74.5 |
| D186,752 S | | 11/1959 | Dean |
| 3,036,962 A | | 12/1959 | McNutt |
| 3,045,321 A | | 7/1962 | McDermott |
| 3,079,669 A | | 3/1963 | Bryant |
| 3,279,043 A | | 10/1966 | Wirt |
| 3,600,803 A | | 8/1971 | Nachel |
| 3,619,878 A | | 11/1971 | Benis et al. |
| 3,636,625 A | | 1/1972 | Pracht |
| 3,738,879 A | | 6/1973 | Von Siemens |
| 3,762,243 A | | 10/1973 | Borrkfield |
| 3,797,505 A | | 3/1974 | Gilhaus et al. |
| 3,905,080 A | | 9/1975 | Bond |
| 4,037,793 A | | 7/1977 | Puustinen |
| 4,057,053 A | | 11/1977 | Kunz |
| 4,075,919 A | | 2/1978 | Komura et al. |
| 4,099,935 A | | 7/1978 | Bond et al. |
| 4,124,437 A | | 11/1978 | Bond et al. |
| 4,126,510 A | | 11/1978 | Moscony et al. |
| D251,103 S | | 2/1979 | Puustinen |
| 4,240,806 A | | 12/1980 | Frantzen |
| 4,256,156 A | | 3/1981 | Biszantz et al. |
| 4,283,820 A | | 8/1981 | Willinger |
| 4,411,597 A | | 10/1983 | Koffel et al. |
| 4,422,465 A | | 12/1983 | Haga |
| D276,812 S | | 12/1984 | Kanazawa |
| 4,497,686 A | | 2/1985 | Weglin |
| 4,537,207 A | | 8/1985 | Gilhaus |
| 4,790,488 A | | 12/1988 | Borner |
| 4,793,218 A | | 12/1988 | Jordan et al. |
| 5,082,009 A | | 1/1992 | Cromer |
| 5,100,506 A | | 3/1992 | Sturtevant et al. |
| 5,302,234 A | | 4/1994 | Grace et al. |
| 5,522,136 A | | 6/1996 | Larisey |
| 5,564,189 A | | 10/1996 | Lee |
| 5,570,700 A | | 11/1996 | Vogeler |
| 5,653,024 A | | 8/1997 | Cartagenova |
| 5,711,491 A | | 1/1998 | Molo |
| D393,986 S | | 5/1998 | Joergensen |
| 5,832,610 A | | 11/1998 | Chaplick |
| 5,881,735 A | | 3/1999 | Kutnik |
| 5,913,313 A | | 6/1999 | Brunderman |
| 6,142,156 A | | 11/2000 | Brunderman |
| 6,261,031 B1 | * | 7/2001 | Stipe et al. .................. 407/29.15 |
| 6,267,658 B1 | * | 7/2001 | Ali et al. .................. 451/523 |
| D447,391 S | * | 9/2001 | Bodum .................. D7/678 |
| 6,283,978 B1 | | 9/2001 | Cheski et al. |
| 6,363,944 B1 | * | 4/2002 | Stangenberg .................. 132/76.4 |
| 6,481,443 B1 | | 11/2002 | Moore-Johnson et al. |
| D483,910 S | | 12/2003 | O'Brien, II |
| D486,268 S | | 2/2004 | Chien |
| 6,733,595 B1 | | 5/2004 | Grillo |
| D491,774 S | | 6/2004 | Brousseau et al. |
| D494,026 S | | 8/2004 | Brousseau et al. |
| D499,313 S | | 12/2004 | Lawson et al. |
| D523,143 S | | 6/2006 | Anderson et al. |
| 7,093,603 B2 | | 8/2006 | Han |
| D549,878 S | | 8/2007 | Kotte |
| D550,522 S | | 9/2007 | Raia |
| D554,801 S | | 11/2007 | Kotte |
| D568,118 S | | 5/2008 | Chalfant et al. |
| D582,097 S | | 12/2008 | Hollinger |
| D596,353 S | | 7/2009 | Yang |
| D596,802 S | | 7/2009 | Yang |
| 2002/0087167 A1 | | 7/2002 | Winitsky |
| 2004/0117935 A1 | * | 6/2004 | Cavalheiro .................. 15/244.1 |
| 2005/0061343 A1 | | 3/2005 | Ebner |
| 2006/0178676 A1 | | 8/2006 | Anderson et al. |
| 2007/0000566 A1 | | 1/2007 | Gueret |
| 2007/0119995 A1 | * | 5/2007 | Yamanaka et al. .................. 241/95 |
| 2007/0214557 A1 | | 9/2007 | Qiu |
| 2008/0000490 A1 | | 1/2008 | Jo |
| 2008/0045974 A1 | | 2/2008 | Dixon |
| 2008/0091216 A1 | | 4/2008 | Grace et al. |

FOREIGN PATENT DOCUMENTS

| | | |
|---|---|---|
| GB | 783479 | 9/1957 |
| GB | 845832 | 8/1960 |
| JP | 56052127 | 5/1981 |
| JP | 56112475 | 9/1981 |
| JP | 56112476 | 9/1981 |
| JP | 56163270 | 12/1981 |
| KR | 20030096747 | 12/2003 |
| WO | WO 03024290 | 3/2003 |
| WO | WO 2004075764 | 9/2004 |
| WO | WO 2006068638 | 6/2006 |

OTHER PUBLICATIONS

English language abstract of West German Patent Publication No. DE 19624578, esp@cenet database, Jan. 8, 1998.
English language abstract of West German Patent Application No. DE 3320594, esp@cenet database, Dec. 13, 1984.
English language abstract of Republic of Korea Patent Publication No. KR 20030096747, esp@cenet database, Dec. 31, 2003.
English language abstract of Japan Patent Publication No. JP 56052127, esp@cenet database, May 11, 1981.
English language abstract of Japan Patent Publication No. JP 56112475, esp@cenet database, Sep. 4, 1981.
English language abstract of Japan Patent Publication No. JP 56112476, esp@cenet database, Sep. 4, 1981.
English language abstract of Japan Patent Publication No. JP 56163270, esp@cenet database, Dec. 15, 1981.
"Nutmeg Grater", 4 pages, <http://www.silvercollection.it>, before 2007.
Summary Information of European Design No. 000527940-0001, 2 pages, <http://oami.europa.eu>, RCD-Online database, Jun. 27, 2006.
"Comfort Callus Rasp", 1 page, <www.tweezerman.com>, 2005.
"Microplane Personal Care", instruction sheet, 1 page, 2008.
English language translation of Japan Patent Publication No. JP 5652127, May 11, 1981.
English language translation of Japan Patent Publication No. JP 56112475, Sep. 4, 1981.
"Replaceable Cartridge for XL Pro Foot File", 2 pages, <www.microplane.com>,2006.
"Transform Your Soles!", 2 pages, <www.microplane.com>, 2005.
"CVS Pumice Stone" and package, 1 page.
"Neat Feet Trim Pumice Stone" and package, 1 page.
"Silly Putty—The Original" and package, 1 page.
"L'eggs" and package, 1 page.
"Parmenide design Alejandro Ruiz" and package, 2 pages.
"Cheese Grater by Bodum.com" and package, 2 pages.
"Cheese Grater Parmesanreibe—Thomas Rosenthal Group" and package, 2 pages.
"Pedicure Tool by Avon Products Inc.", 2 pages.
"Smooth Touch for Soft Sassy Feet" and package, 4 pages, TV Products USA, 2008.
Broussard, M. "Foot for Thought." Apr. 17-23, 2003. archives.citypaper.net/articles/2003-04-17/cover5.shtml.

\* cited by examiner

SKIN REMOVING IMPLEMENT

CROSS-REFERENCE TO RELATED APPLICATIONS

This application is a continuation-in-part of prior application Ser. No. 29/292,718 filed Oct. 25, 2007 now abandoned and prior application Ser. No. 29/292,719 filed Oct. 25, 2007 now abandoned, both applications hereby incorporated by reference.

This application also hereby incorporates by reference People's Republic of China Application No. 2007 30309021.2 filed Sep. 14, 2007.

BACKGROUND OF THE INVENTION

Field of the Invention

This invention relates generally to the field of skin removing files and rasps.

Description of the Related Art

Many products have been created to remove excess skin, such as calluses, from a person's foot. Many of these devices comprise a rasp, file or plane attached to the end of a handle such that the user can hold one end of the device and rub the other end across the area of skin that is to be removed. However, these devices are inconvenient because these devices do not capture the skin once removed from the person's body, but instead allow the skin to fall to the ground thereby requiring the user to clean the entire area where the device was used.

Moreover, conventional foot rasps, files and planes leave the operative surface exposed when the device is not in use which may be unsanitary. Furthermore, the operative surface of such conventional devices can damage the area where the device is stored since the abrasive and/or cutting surface is left exposed at all times.

One conventional foot file attempts to overcome these problems by placing the cutting surface at one end of a hollow chamber and sealing the other end of the chamber with a removable cover such that removed skin will be retained by the chamber. This removable cover also can be placed over the cutting surface to shield a user or storage surface from the cutting surface. However, with this device the cutting surface cannot be covered without leaving the chamber open, thereby allowing removed skin pieces to fall out.

Accordingly, a skin removal implement should desirably have a way to collect skin after removal and should also provide a way to protect the user, as well as a storage surface, from the cutting surface when the device is not actively being used.

SUMMARY OF THE INVENTION

An object of the present invention is to provide a skin removing implement that collects and stores removed skin while the implement is in use.

An additional object of the present invention is to store removed skin within the implement when the device is not in active use.

Another object of the present invention is to protect the user's hand from abrasions while the device is being used to remove dead or rough skin.

Yet another object of the present invention is to provide a skin removing device with a file that can be cheaply and easily replaced.

To these and other ends, the present invention broadly contemplates a skin removal implement having a cartridge which forms a frame with a front and a back side, wherein a file with cutting edges is attached to the front side of the cartridge and a removable handle having a sidewall, an end wall and an open face is connected to the back side of the cartridge such that a cavity is formed between the front side of the cartridge and the end wall of the handle. When the file is moved across a person's skin, small pieces of skin are cut off the person's body by the cutting edge and are collected in the chamber formed by the cartridge and the handle. A cover can be removably attached over the front side of the cartridge to shield a user, and/or a storage surface, from the cutting edge when the implement is not in use. The cover also prevents shaved off pieces of skin from leaking out of the chamber through the cutting edge holes when the device is not in use.

In one embodiment of the present invention, the cover has an abrasive surface attached to its outside end which can also be used to remove skin from a person by rubbing the abrasive surface across the area of skin that is to be removed.

DETAILED DESCRIPTION OF THE PREFERRED EMBODIMENT

Figure 1:
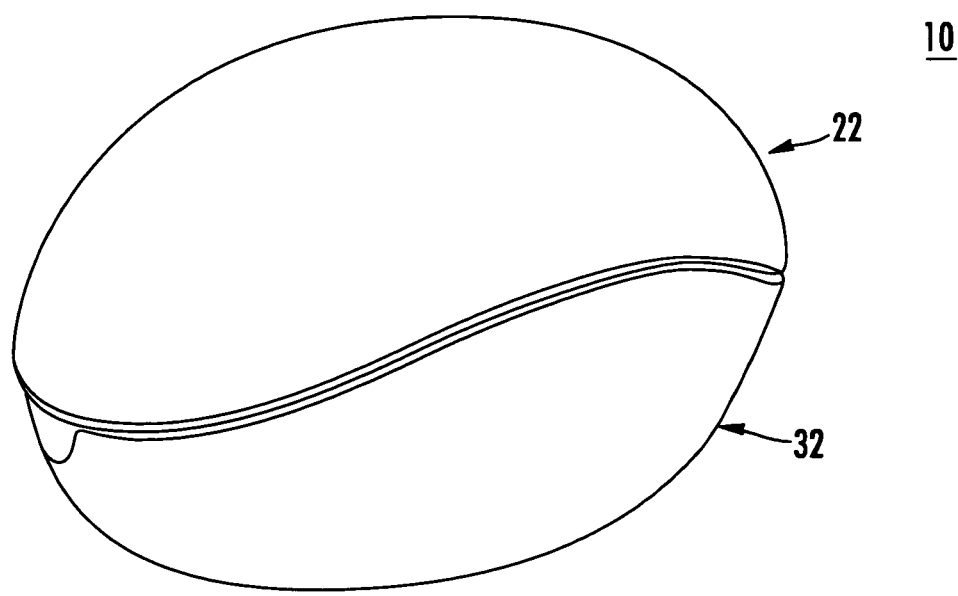
FIG. 1 is a perspective view of the skin removing implement with the cover attached according to one embodiment of the present invention.
Figure 2:
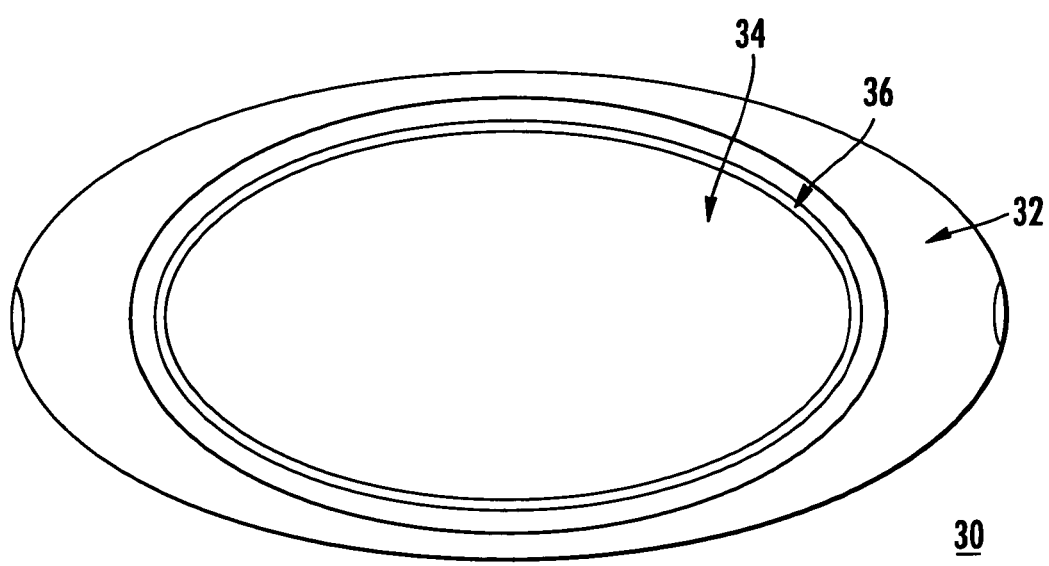
FIG. 2 is a bottom view of the skin removing implement with the cover attached according to one embodiment of the present invention.
Figure 3:
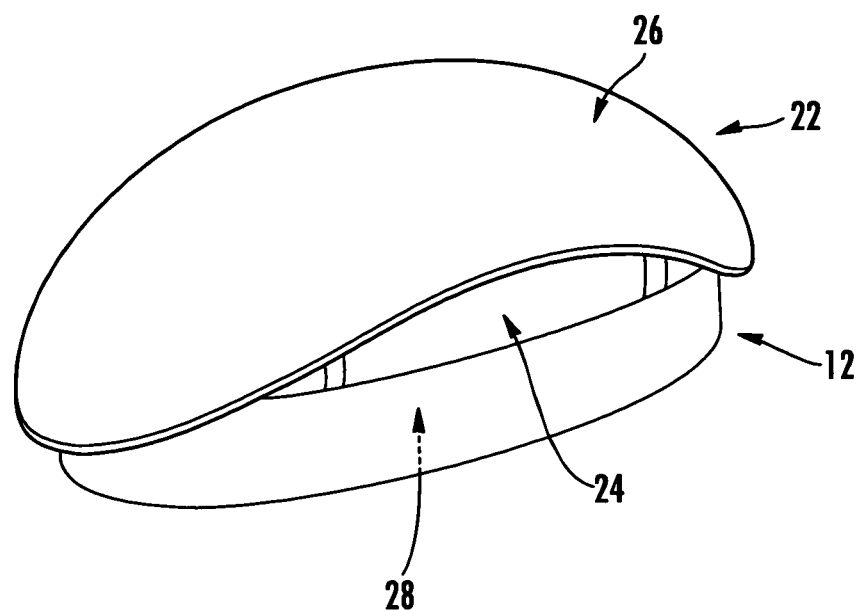
FIG. 3 is a perspective view of the skin removing implement with the cover removed according to one embodiment of the present invention.
Figure 4:
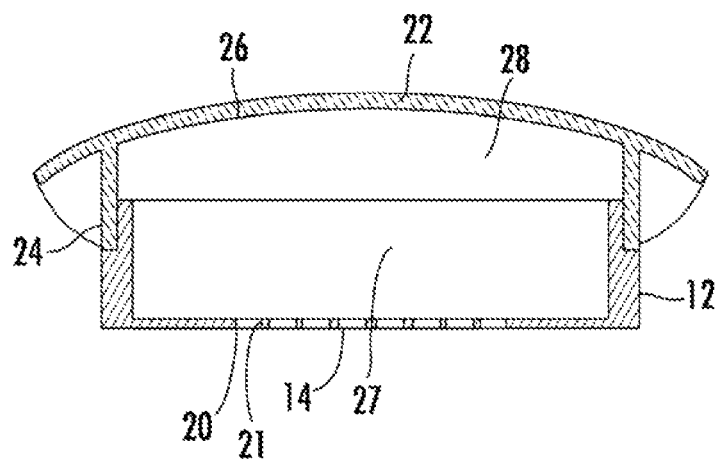
FIG. 4 is a cross-sectional view of the skin removing implement with the cartridge attached to the handle according to one embodiment of the present invention.
Figure 5:
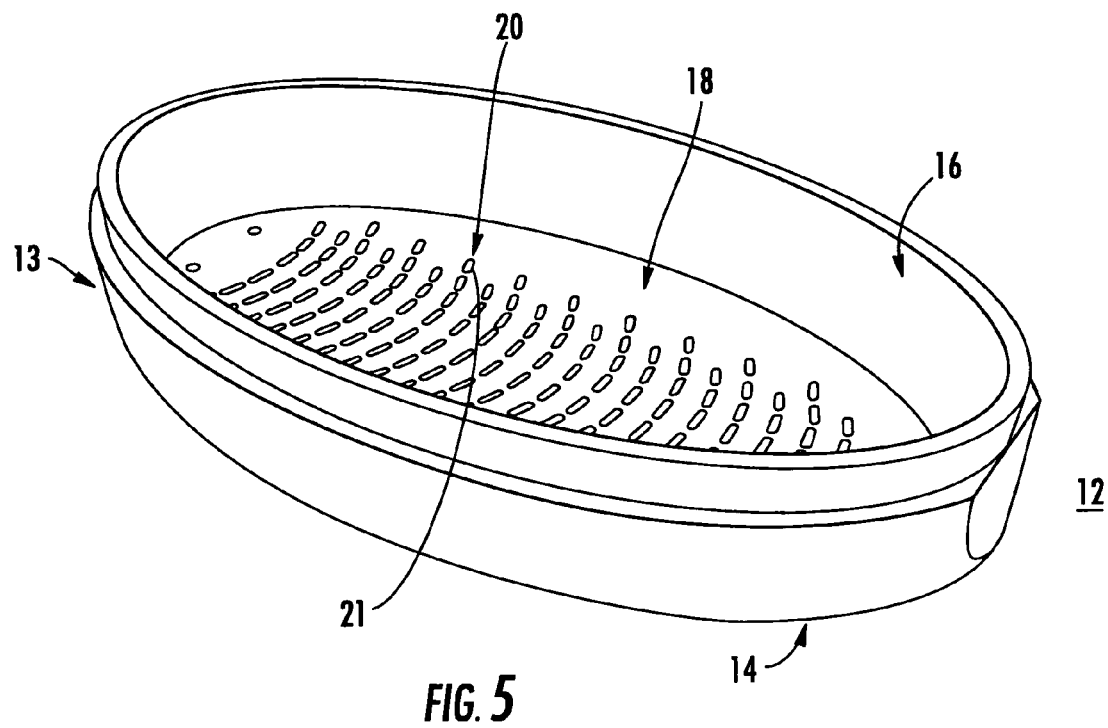
FIG. 5 is a perspective view of the file cartridge of the skin removing implement according to one embodiment of the present invention.
Figure 6:
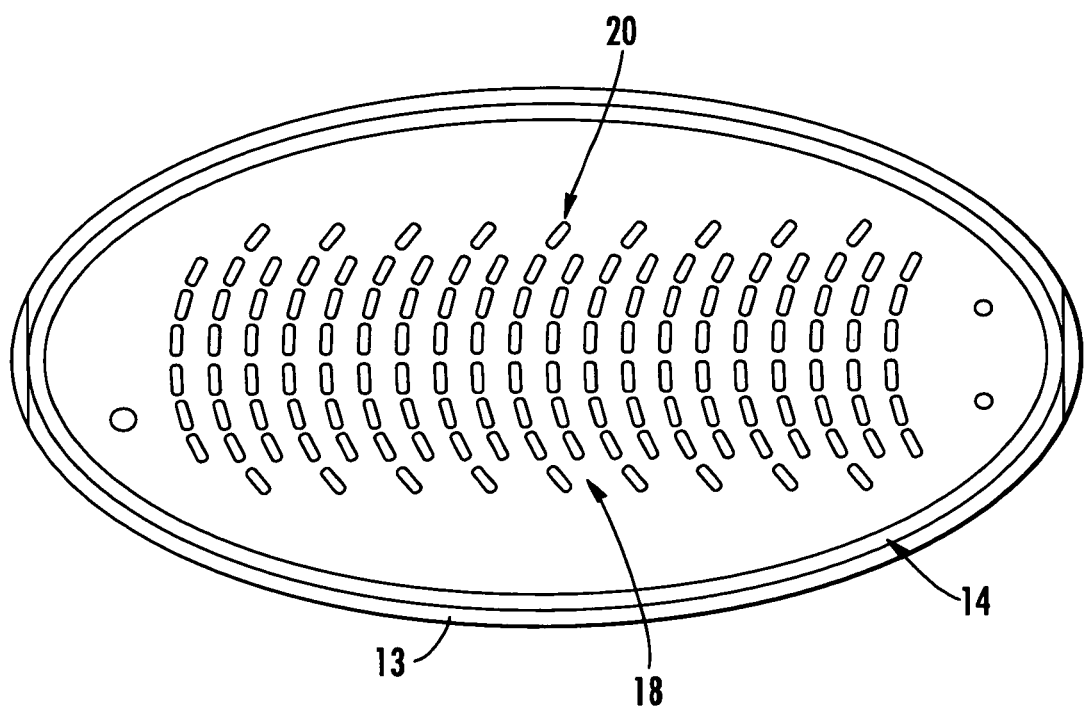
FIG. 6 is a bottom view of the file cartridge according to one embodiment of the present invention.
Figure 7:
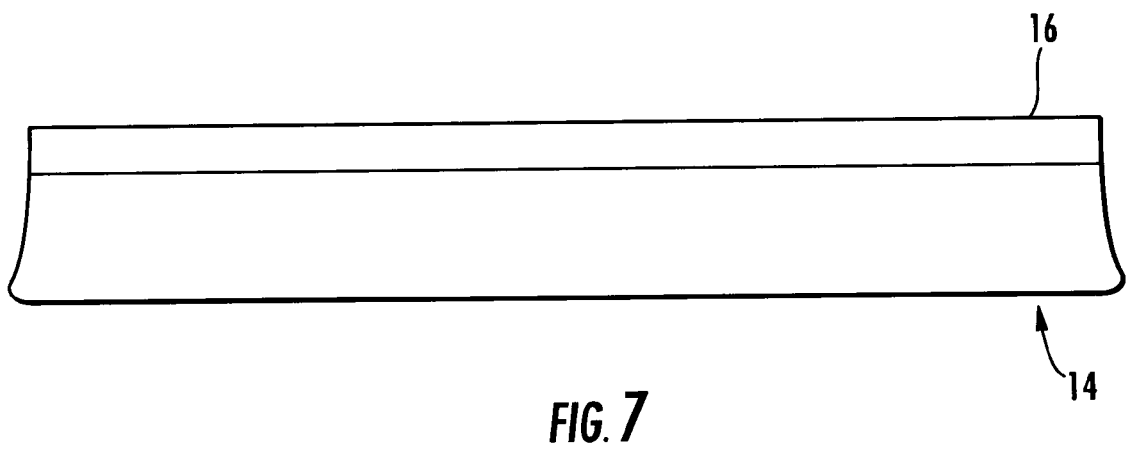
FIG. 7 is a side view of the file cartridge according to one embodiment of the present invention.

A skin removing implement according to one embodiment of the present invention will be discussed with reference to the attached FIGS. 1-6. The skin removing implement 10 includes a cartridge 12 which is formed as a frame 13 with a front side 14 and a back side 16. A file 18 having a plurality of cutting edges 20 and respective proximate holes 21 is connected to the front side 14 of the cartridge while a handle 22 can be removably connected to the back side 16 of the cartridge 12. The handle 22 has a sidewall 24, an end wall 26 and an open end 27 on the side that faces the back side 16 of the cartridge 12 such that a chamber 28 is formed between the front side 14 of the cartridge 12 and the end wall 26 of the handle 22 when the handle is attached to the cartridge. This configuration is advantageous as the removed skin will be conveniently collected within the chamber 28.

The skin removing device 10 also has a cover 30 that is removably attached to the handle 22. The cover 30 has an inner side (not shown) which faces the cartridge 12 and an outer side 32 which is exposed to the user when the cover 30 is connected to the handle 22. When the cover 30 is attached to the handle 22, the cutting edges 20 are hidden from contact with a user and/or a storage surface.

To use the skin removing implement 10 to remove unwanted skin, a user attaches handle 22 to cartridge 12, removes cover 30, and runs the file 18 across the skin that is to be removed. This action will cause the cutting edges 20 to cut off small pieces of skin which can then fall through the holes 21 in the front side 14 of the cartridge 12 and collect in chamber 28. This process can be repeated until the desired amount of skin has been removed. The user can then detach handle 22 from the cartridge 12, discard the removed skin from the chamber 28, and reattach the cartridge to the handle.

In one embodiment, the cartridge 12 can be replaced by the user. Replacing the cartridge may be beneficial if the cutting edges 20 of the file 18 become dull and/or damaged or if the holes 21 become permanently clogged with removed skin or other detritus. This configuration is advantageous as it allows the file 18 to be changed without requiring the entire skin removing implement 10 to be replaced.

In one embodiment, the outer side 32 of cover 30 contains an abrasive surface 34. This abrasive surface 34 can be used to remove skin by rubbing the surface 34 against the area of skin that is to be removed. The outer side 32 of cover 30 may also contain a contact rim 36 which is raised above the abrasive surface 34 such that only the contact rim 36, and not the abrasive surface 34, will contact the surface upon which the skin removal implement 10 is placed. This configuration is advantageous because the skin removal implement 10 can be stored without abrading the storage surface.

To protect the user from injury by the file 18 while the skin removing implement 10 is not actively being used or the abrasive surface is being used, the cover 30 can be attached to the handle 22 such that the cutting edges 20 are shielded by the cover 30 and will not contact the user. As a further benefit, the cover 30 in this position will also prevent removed skin located in chamber 28 from falling back through the holes 21 and out the front side 14 of cartridge 12.

It is to be understood that the invention is not limited to the features and embodiments hereinabove specifically set forth, but may be carried out in other ways without departure from its spirit.

What is claimed is:

1. A device for removing skin, comprising:
a cartridge formed as a frame having a front side and a back side and a file supported by the frame at said front side, the file having a plurality of cutting edges for scraping skin from a person's body at the front side of the frame, and respective proximate holes through which removed skin passes toward the back side of the frame;
a handle having a side wall, an end wall and an open end removably attachable to the cartridge with the open end of the handle facing the back side of the frame to form a chamber for storing removed skin, said handle being manually graspable for moving the file across a person's skin, said end wall curving convexly outward in a direction away from said open end; and
a cover having an inner side and an outer side, removably connectable to the cartridge with said inner side facing the front side of the cartridge and cooperating with the handle to completely enclose the file on both the front and back sides of the frame, thereby to prevent stored removed skin from leaking out of the chamber;
further comprising an abrasive surface on the outer side of the cover and a rim raised on the cover above the abrasive surface such that the abrasive surface will not contact a storage surface when the cover is placed on the storage surface.

\* \* \* \* \*